(12) United States Patent
Schub

(10) Patent No.: US 11,234,714 B2
(45) Date of Patent: Feb. 1, 2022

(54) COMBINATION SURGICAL DRILL AND REMOTE GRASPING DEVICE

(71) Applicant: David Schub, Rancho Santa Fe, CA (US)

(72) Inventor: David Schub, Rancho Santa Fe, CA (US)

(73) Assignee: Schrilla, LLC, Rancho Santa Fe, CA (US)

( * ) Notice: Subject to any disclaimer, the term of this patent is extended or adjusted under 35 U.S.C. 154(b) by 238 days.

(21) Appl. No.: 16/798,311

(22) Filed: Feb. 22, 2020

(65) Prior Publication Data

US 2021/0106343 A1 Apr. 15, 2021

Related U.S. Application Data

(60) Provisional application No. 62/914,858, filed on Oct. 14, 2019.

(51) Int. Cl.
*A61B 17/16* (2006.01)
*A61B 17/29* (2006.01)

(52) U.S. Cl.
CPC .......... *A61B 17/1615* (2013.01); *A61B 17/29* (2013.01); *A61B 17/1628* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1631; A61B 17/1633; A61B 17/29; A61B 17/2909; A61B 17/295; A61B 2017/2926; A61B 2017/2627; A61B 2017/2929
See application file for complete search history.

(56) References Cited

U.S. PATENT DOCUMENTS

| | | | | |
|---|---|---|---|---|
| 4,836,205 A | * | 6/1989 | Barrett | A61B 17/0469 606/144 |
| 10,166,030 B2 | * | 1/2019 | Newell | A61B 17/3201 |
| 2015/0216515 A1 | * | 8/2015 | Newell | A61B 17/1622 606/1 |
| 2021/0106343 A1 | * | 4/2021 | Schub | A61B 17/1633 |

* cited by examiner

*Primary Examiner* — Eric S Gibson
(74) *Attorney, Agent, or Firm* — Justin Lampel

(57) ABSTRACT

A surgical instrument is provided. The surgical instrument has a drill bit employable in drilling procedures wherein the drill bit is made of a plurality of radially positioned drill bits which also may be utilized as a grasping device. As a result, the drill bit may not only drill into bone, but may also be used to grasp an object, such as a portion of the body. The present surgical instrument reduces contamination which may otherwise result from switching surgical instruments from a drill to a grasping mechanism or from the need to drill multiple holes into the patient's body.

14 Claims, 7 Drawing Sheets

COMBINATION SURGICAL DRILL AND REMOTE GRASPING DEVICE

CROSS REFERENCE TO RELATED APPLICATIONS

The following application is a based on and claims the priority benefit of U.S. provisional application Ser. No. 62/914,858 filed Oct. 14, 2019; the entire content of which is incorporated by reference.

BACKGROUND OF THE INVENTION

A surgical instrument is provided. The surgical instrument has a drill bit employable in drilling procedures wherein the drill bit is made of a plurality of radially positioned drill bits which also may be utilized as a grasping device. As a result, the drill bit may not only drill into bone, but may also be used to grasp an object, such as a portion of the body. The present surgical instrument reduces contamination which may otherwise result from switching surgical instruments from a drill to a grasping mechanism or from the need to drill multiple holes into the patient's body.

BACKGROUND OF THE INVENTION

During the performance of surgical procedures, there are often situations which require that a tunnel be drilled through, for example, a patient's bone to allow access to another compartment or space within the body, such as a joint space. This is something which is commonly encountered in arthroscopic surgery in orthopedics. In these procedures, there are generally small incisions made in the patient's skin to access spaces within the body that are in need of repair.

During such procedures, the surgeon will frequently drill a passage which communicates completely through a bone structure of the patient, and in a subsequent surgical step, the surgeon will frequently employ secondary instruments to feed a required component through the passage previously formed by the drill.

This conventional mode of drilling and subsequent feeding of a secondary component through the formed passage, currently requires that a surgical drill be communicated through one body entry point on the patient. To complete the task of feeding a part or component through the drilled passage, the surgeon must then either remove the drill from its entry point in the patient and insert a secondary instrument for grasping, in order to feed a secondary component through the formed passage, or the surgeon must form a secondary entry point into the body of the patient for positioning of the grasping instrument.

Both options required multiple actions by a skilled surgeon extending the duration of the surgical procedure. Further, forming multiple passages into the body of the patient is less than desirable and potentially increases recovery time and risk of infection due to the formation of such multiple access points.

The forgoing examples of related art in the field of orthopaedic surgery and limitations related therewith are intended to be illustrative and not exclusive, and they do not imply any limitations on the presently described combination surgical drill and remote grasping device. Various limitations of the related art will become apparent to those skilled in the art upon a reading and understanding of the specification below and the accompanying drawings.

SUMMARY OF THE INVENTION

A surgical instrument is provided. The surgical instrument has a drill bit employable in drilling procedures wherein the drill bit is made of a plurality of radially positioned drill bits which also may be utilized as a grasping device. As a result, the drill bit may not only drill into bone, but may also be used to grasp an object, such as a portion of the body. The present surgical instrument reduces contamination which may otherwise result from switching surgical instruments from a drill to a grasping mechanism or from the need to drill multiple holes into the patient's body.

The combination drill and grasping instrument system herein disclosed and described provides a solution to the shortcomings in prior art noted above. It achieves the above noted goals through the provision of a surgical drill configured while the instrument is in a closed configuration, to form openings and passages in the bones of a patient in a conventional fashion. The drill portion of the device is additionally configured during operative control by the surgeon to form a grasping tool which expands the drill bit into a plurality of sections to allow the surgeon to remotely grasp a secondary component or device. Thus, the combination drill and grasping device herein is employable, for example, by a surgeon in a first step to drill through and form a passage through bone. Subsequent to completion of the first step, with the drill bit communicating through a distal end of the passage, in a second step, the surgeon can operate the device to expand the drill bit to a plurality of spaced bit portions, to grasp and pull a device or component backwards through the hole just formed by the drill.

By configuring the device herein in a manner enabling its employment for two tasks during a surgery, multiple entry points into a patient for surgery can be reduced or eliminated, thus making the procedure itself less trying upon the patient. Further, in instances where a component must be pulled back through a previously drilled hole, the present instrument saves significant time for the surgeon, since he/she no longer must employ a secondary grasping instrument to "fish" for the component after feeding that instrument through the drilled hole.

With respect to the above description, before explaining at least one preferred embodiment of the herein disclosed combination drill and grasping instrument in detail, it is to be understood that the invention is not limited in its application to the details of construction and to the arrangement of the components in the following description or illustrated in the drawings. The invention herein described is capable of other embodiments and of being practiced and carried out in various ways which will be obvious to those skilled in the art. Also, it is to be understood that the phraseology and terminology employed herein are for the purpose of description and should not be regarded as limiting.

As such, those skilled in the art will appreciate that the conception upon which this disclosure is based, may readily be utilized as a basis for designing and configuring other drill and grasping instruments employed for surgery (or even outside of surgery), and for carrying out the several purposes of the presently disclosed device. It is important, therefore, that the claims be regarded as including such equivalent construction and methodology insofar as they do not depart from the spirit and scope of the present invention.

As used in the claims to describe the various inventive aspects and embodiments, "comprising" means including, but not limited to, whatever follows the word "comprising". Thus, use of the term "comprising" indicates that the listed elements are required or mandatory, but that other elements are optional and may or may not be present. By "consisting of" is meant including, and limited to, whatever follows the phrase "consisting of". Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Finally, unless provided with a specific different respective definition, the term "substantially" herein, means plus or minus five percent. It is an object of this invention to provide a surgical instrument configured for both drilling and for grasping. It is a further objection of the invention to provide such a device which will shorten surgery times and lessen the physical impact on patients by reducing the number of body entry points and steps required during surgery. These and other objects of the combination surgical drill and grasping instrument herein, will be brought out in the following part of the specification, wherein detailed description is for the purpose of fully disclosing the invention without placing limitations thereon.

BRIEF DESCRIPTION OF DRAWING FIGURES

The accompanying drawings, which are incorporated herein and form a part of the specification, illustrate some, but not the only or exclusive, examples of embodiments and/or features of the surgical instrument. It is intended that the embodiments and figures disclosed herein are to be considered illustrative rather than limiting.

DETAILED DESCRIPTION OF THE PREFERRED EMBODIMENTS OF THE INVENTION

Figure 1:
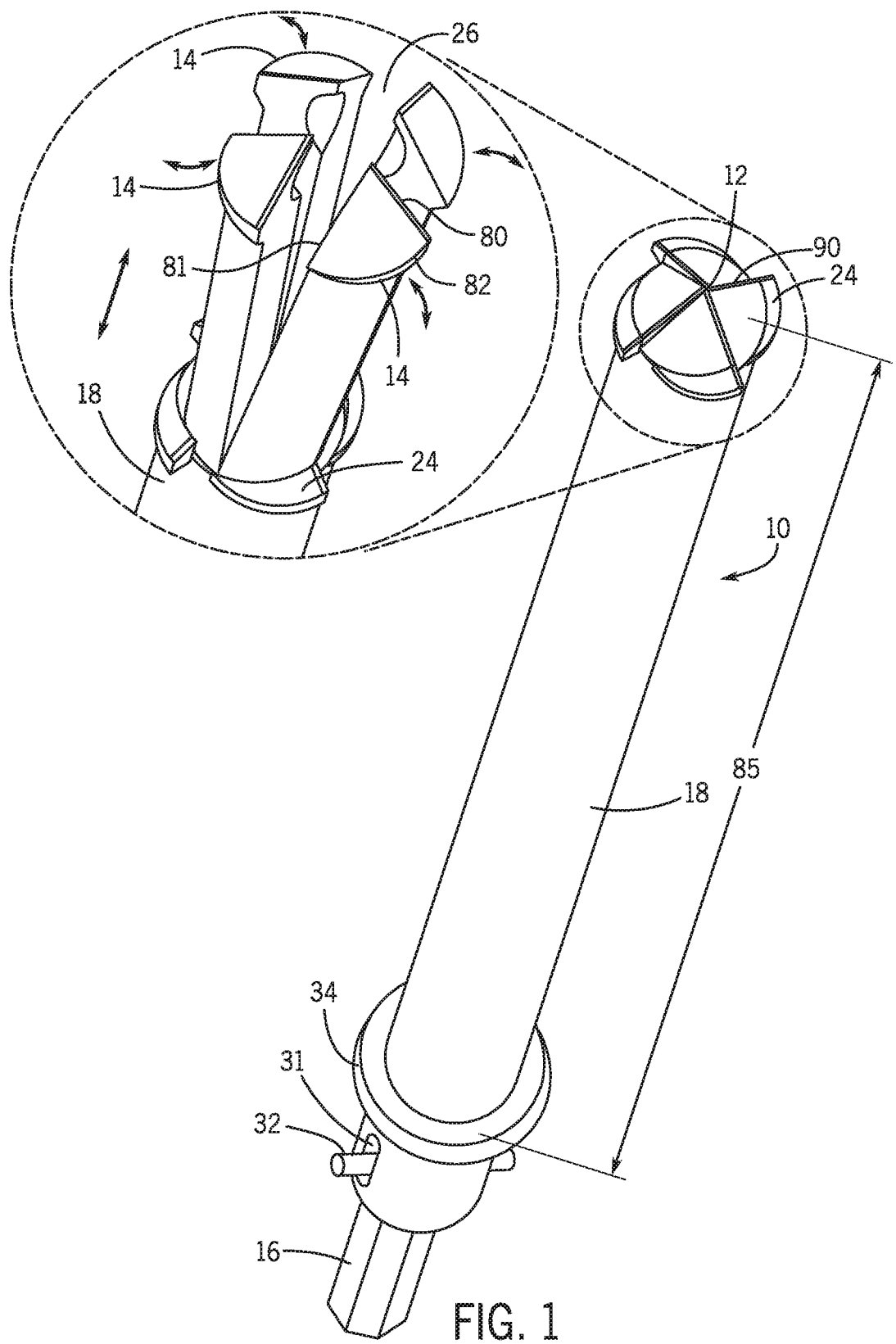
FIG. 1 depicts a perspective view of the combination drill bit and grasping instrument in one embodiment, showing the drill bit in a collapsed position within a supporting sheath and moveable to an expanded position (shown close-up) which is employable for grasping.

A surgical instrument is provided. The surgical instrument has a drill bit employable in drilling procedures wherein the drill bit is made of a plurality of radially positioned drill bits which also may be utilized as a grasping device. As a result, the drill bit may not only drill into bone, but may also be used to grasp an object, such as a portion of the body. The present surgical instrument reduces contamination which may otherwise result from switching surgical instruments from a drill to a grasping mechanism or from the need to drill multiple holes into the patient's body.

In this description, the directional prepositions of up, upwardly, down, downwardly, front, back, top, upper, bottom, lower, left, right and other such terms refer to the device as it is oriented and appears in the drawings and are used for convenience only. They are not intended to be limiting or to imply that the device has to be used or positioned in any particular orientation.

Figures 2A, 2B:
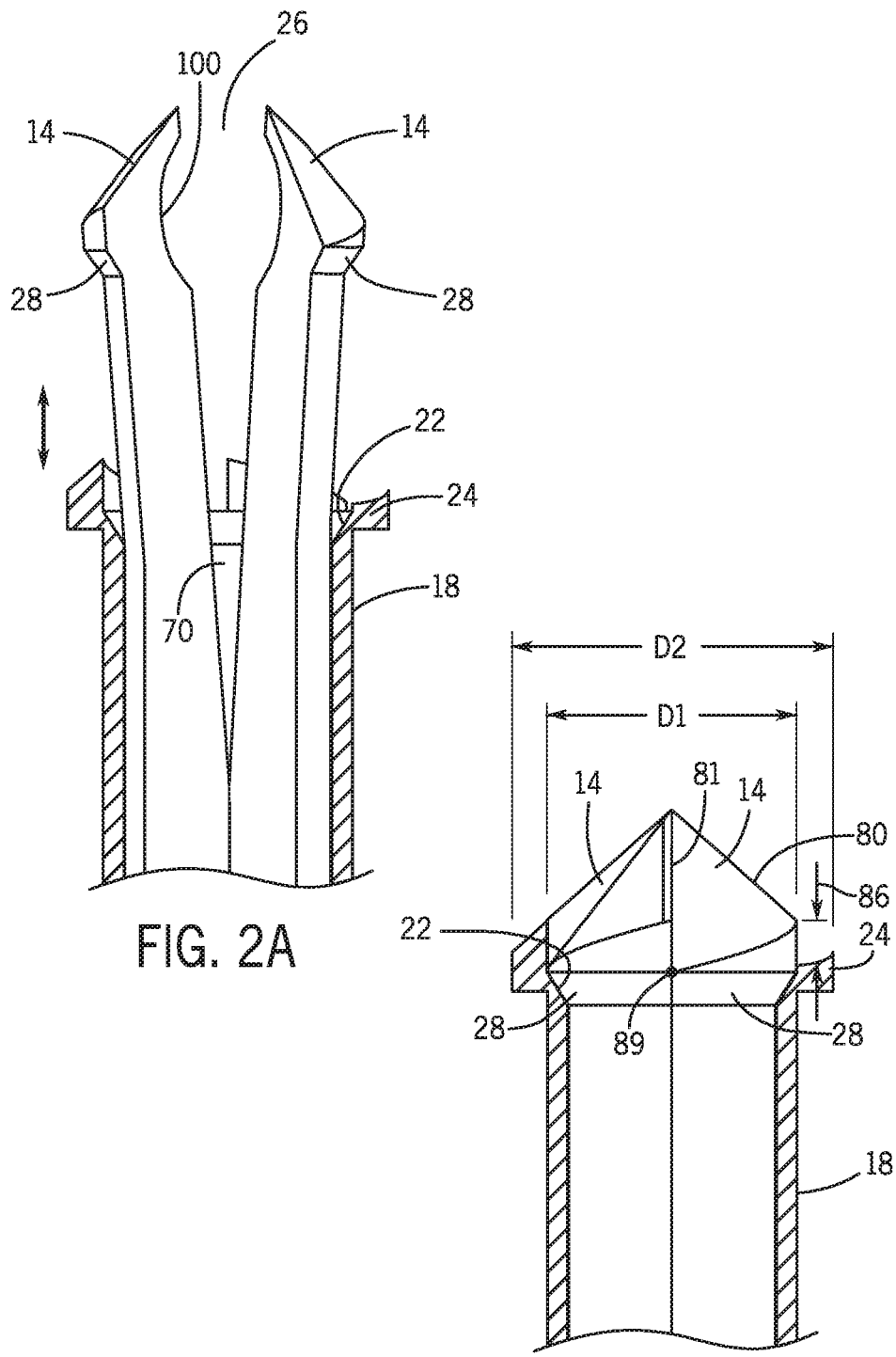
FIG. 2A depicts a sectional view through showing the drill bit in the expanded position, projecting from the flared opening at the distal end of the support sheath in one embodiment.
FIG. 2B depicts a sectional view similar to that of FIG. 2A, but showing the drill bit collapsed (or 'retracted') into the opening formed at the distal end of the support sheath wherein the instrument is employable for drilling in one embodiment.

Referring first to FIG. 1, in an embodiment, a perspective view of the surgical instrument 10 is provided. The surgical instrument 10 may have a drill bit portion 12 and a sheath 18 portion wherein the drill bit portion 12 may move with respect to the sheath portion 18 between a collapsed orientation (FIG. 2B) and an expanded orientation (FIG. 2A). FIG. 1 illustrates the surgical instrument 10 in both the collapsed orientation wherein only the top of the drill bit is visible (wherein the shaft of the drill bit is concealed by the sheath 18) and further illustrates the drill bit in the expanded orientation (in the enlarged depiction). In the collapsed orientation the surgical instrument 10 is suitable for drilling and in the expanded orientation the surgical instrument 10 is suitable for grasping an object.

The surgical instrument 10 may be made of, for example, metal, rubber and/or plastic components. Preferably, the surgical instrument 10 is durable, resistant to corrosion and is easily sterilizable for repeat usage. The drill bit portion 12 of the surgical instrument 10 may be comprised of a plurality of radially position individual drill bit sections 14 (resembling pie pieces in the drawings) and wherein the drill bit sections 14 may move independent of and/or with respect to each other. The figures illustrate four drill bit sections 14 forming the completed drill bit 12; however, a greater or a fewer number of drill bit sections 14 may be used to create the completed drill bit 12.

Figure 5:
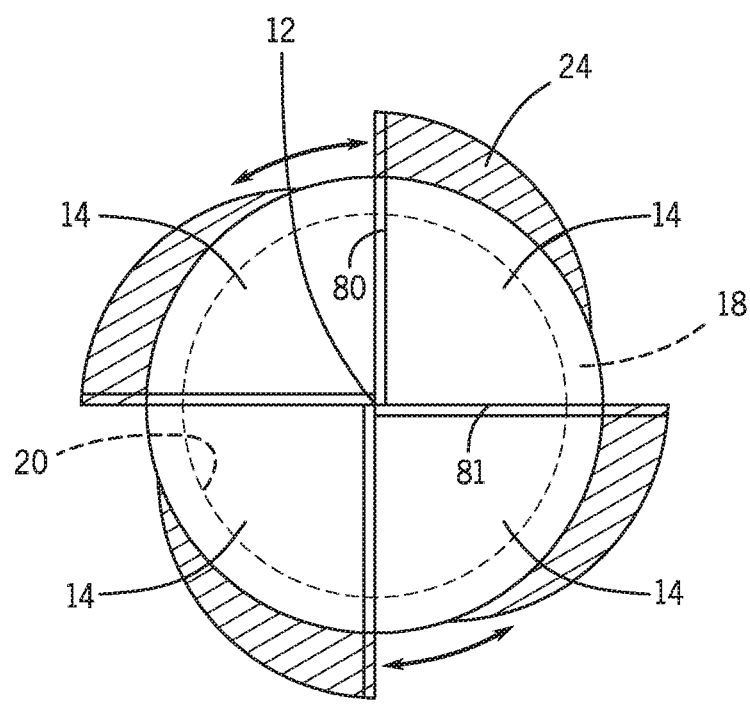
FIG. 5 depicts a view of the distal (or terminal) end of the surgical instrument device in one embodiment showing a particularly favored engagement of the contact areas of the bit portions forming the drill, with the interior surface defining the opening of the support sheath at a distal end thereof.
Figure 7:
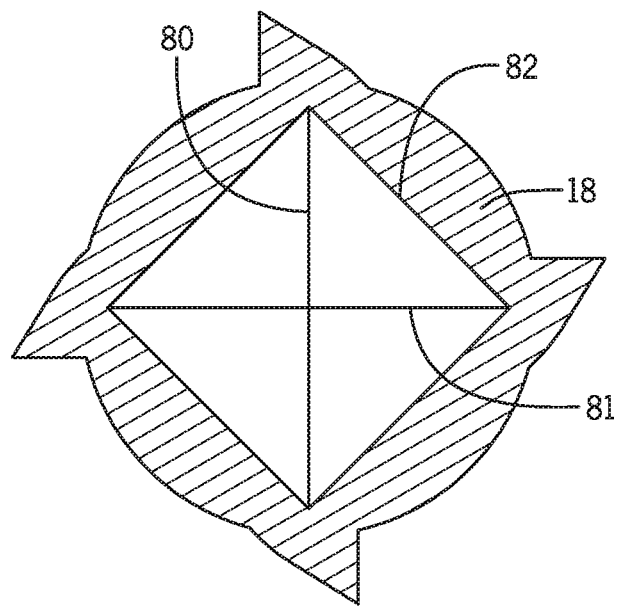
FIG. 7 illustrates a top view of the instrument in the preferred embodiment wherein the drill bit is square-shaped and wherein the drill bit is located within the sheath.

In an embodiment, each of the drill bit sections 14 may have a first interior side 80, a second interior side 81 and an exterior side 82; therein generally forming a pie-piece shaped triangle in the circular embodiment (FIG. 5) or the triangle-shaped exterior side 82 in the preferred embodiment (FIG. 7). In an embodiment, the first interior side 80 and the second interior side 81 are generally flat such that when the drill bit 12 is in the collapsed orientation (FIG. 2B) the plurality of drill bit sections 14 align with each other and are generally flush with each other forming a substantially complete circle when viewed from the top (as shown in FIG. 5). In an embodiment, the exterior sides 82 of the plurality of drill bit sections 14 may be generally curved, generally forming a complete circle when the drill bit 12 is in the collapsed orientation shown in FIG. 5.

In an embodiment, the plurality of drill bit sections 14 are supported by a support sheath 18 having an interior 70 (FIG. 2A). The interior 70 of the support sheath 18 may be cylindrical (FIG. 5) or square-shaped (FIG. 7) in the preferred embodiment. The shaft of the drill bit 12 may be moved vertically within and with respect to the interior 70 of the sheath 18; wherein a portion of the shaft of the drill bit 12 always is located within the interior 70 of the sheath 18. As the drill bit 12/sections 14 move outward or vertically with respect to the sheath 18, the overall length 85 (FIG. 1) of the surgical instrument 10 becomes greater. Conversely, when the shaft of the drill bit 12 is collapsed (or retracted) into the interior 70 of the sheath 18 the overall length 85 of the instrument 10 is decreased. In the completely collapsed orientation, as shown in FIG. 2B, only the very distal end of the drill bit 12 is visible as the shaft of the drill bit 12 is concealed by the sheath 18.

In the circular configuration, the sheath 18 of the present instrument 10 may have an interior diameter 75 (FIG. 3A) which is slightly greater than a diameter of the shaft of the drill bit 12 when the drill bit 12 is in the collapsed orientation of FIG. 2B. As a result, the drill bit 12 is held in the collapsed orientation by the interior cylindrical wall of the sheath 18 in the circular configuration. In the preferred square-shaped drill bit 12 configuration (FIG. 7), the square interior of the sheath 18 holds the drill bit 12 in the collapsed orientation.

When the surgeon moves the drill bit 12 from the collapsed to the expanded orientation, the restraining pressure from the interior wall of the sheath 18 which holds the drill bit sections 14 together as a single drill bit 12 is released at the terminal end 90 of the drill bit 12 and the plurality of drill bit sections 14 may therein start to move away from each other and may create a gap 26 located between each of the drill bit sections 14 (as shown in FIGS. 1 and 2A). In an embodiment, the distal end of the drill bit sections 14 (the ends of the drill bit sections located away from the handle) may move a greater distance away from each other than the ends of the drill bit sections 14 located next to the handle of the instrument.

As shown in FIG. 1 and other figures herein, the drill bit 12 in the collapsed configuration of the instrument 10 is adapted to rotate under power provided from a drill motor 426 (FIG. 6) located within a handle 427. More specifically, a drive member 16 of the surgical instrument 10 may be connected/attached to the drill motor 426 which rotates the drill bit 12 at high velocity for drilling into, for example, bone during an operation. In this collapsed configuration, and employable to drill openings in the body, the support sheath 18 is in biased contact at an opening 20 (FIG. 5), against contact points with the individual plurality of radially disposed drill bit portions 14. While other configuration will hold the drill bit portions 14 in a collapsed orientation, in a particularly preferred mode of the surgical instrument 10, a beveled portion 22 (FIG. 2A) of the support sheath 18 surrounds and contacts each of the exterior sides 82 of the plurality of bit portions 14 at a contact surface 28 on the drill bit portions 14.

In the collapsed orientation of 2B, the drill motor rotates the drill 12 so that a surgeon may drill into, for example, bone of a patient. In all preferred modes of the surgical instrument 10 herein, the support sheath 18 is biased toward and into the plurality of bit portions 14 to maintain them collapsed and ready to drill.

In an embodiment, the instrument 10 may have a plurality of cutting spurs 24 projecting radially from the distal end of the support sheath 18 in a direction away from the opening 20 of the support sheath 18. While the surgical instrument 10 will perform well without these cutting spurs 24, it is preferred they be included in the favored mode. These cutting spurs 24 act to enlarge the diameter of the hole or passage formed by the surgical instrument 10 during drilling, to a diameter slightly larger than the diameter of the drill 12 formed by the collapsed bit portions 14. Such is shown in FIG. 2B and described below. In an embodiment, the sheath 18 rotates along with the drill bit 12. The spurs 24 of the sheath 18 also rotates as they are permanently attached to the sheath 18. In an embodiment, the spurs 24 are generally perpendicular to the sheath 18.

Shown in FIG. 2A is a sectional view depicting bit portions 14 in the expanded configuration where the drill bit sections 14 form a grasping instrument for grasping items positioned within the gap 26 therebetween. Once the item to be grasped is positioned within the gap 26, the bit portions 14 may be slightly retracted so that the drill bit portions 14 start to return to the collapsed orientation. In the process of returning to the collapsed orientation, the plurality of drill bit portions 14 will therein contact and secure the object. The object may then be moved by the surgeon. Once the object is moved to the correct location, the surgeon may release the object by then expanding the drill bit portions 14. Preferably, the surgical instrument 10 is returned to the collapsed orientation prior to removal of the surgical instrument 10 from the body (therein reducing the overall diameter of the device), unless the grasped object is to be completely removed from the patient's body. When the drill bit sections 14 move to the expanded orientation, they move along an x-axis with respect to the sheath 18 which remains stationary along the same x-axis.

By returning the drill bit portions 14 back to the collapsed position shown in FIG. 2B, the beveled portions 22 of the sheath 18 then become a biased contact against the contact areas 28 of each of the plurality of radially positioned bit portions 14. Maintaining such a biased or fixed contact of the support sheath 18 against each of the bit portions 14 will maintain the bit portions 14 in the collapsed position to form the drill bit 12 as in FIG. 1 and FIG. 2B.

In an embodiment, near the terminal (or "distal") ends 90 of the plurality of drill bit portions 14 may be an indented portion 100 (FIG. 2A). The indented portions 100 may be an arched-shaped cutout from both the interior first side 80 and interior second side 81 of each of the plurality of drill bit portions 14. The indented portions 100 may allow the drill bit portions 14 to better grasp and/or hook the object when the drill bit 12 of the surgical instrument 10 is in the expanded orientation as shown in FIG. 2A and the instrument is used to grasp an object. In an embodiment, when the plurality of drill bit sections 14 are in the collapsed orientation, the plurality of indented portions 100 of each drill bit section 14 will align and form a concealed hollow pocket within the drill bit 12. The pocket may be used to secure an object and remove the object from the body if necessary.

In an embodiment, both the first side 80 and the second side 81 of each of the plurality of drill bit portions 14 may have a height. As shown in FIG. 2B, in an embodiment, the first side 80 of each of the plurality of drill bit portions 14 may have a height 86 which is greater than a height 89 of the second side 81 of that same drill bit portion 14 so that each drill bit portion 14 is angled. Further, because the first side 80 of one drill bit portion 14 touches the second side 81 of an adjacent drill bit portion 14 the drill bit portions 14 are staggered and result in greater cutting and drilling.

As noted, the distal end of the support sheath 18 may be in substantially planar or straight contact against the bit portions 14. However, currently preferred for enhanced contact of the support sheath 18 with each of the bit portions 14, in a manner better maintaining them in position for and during drilling, is the mating of the shape of the collapsed drill 12 and the contact areas 28 thereon, with the size and shape of the interior surface defining the opening 20 at the distal end of the support sheath 18. This contact area 28 also serves to help use the force generated while the drill bit 12 is rotating and drilling to hold the bit portions 14 together within the sheath 18 and in a collapsed orientation. In FIG. 2B is shown a sectional view similar to that of FIG. 2A, but instead, depicting the drill bit 12 formed by the plurality of bit portions 14 contacting each other in the retracted or collapsed orientation. As noted, the contact of the distal end of the support sheath 18 against the contact areas 28 of each of the bit portions 14, holds them retracted and in a drill bit 12 configuration. In an embodiment, the contact areas 28 form a surface which is approximately at a seventy to one hundred and ten degree angle with respect to the top of each drill bit section 14.

Also shown in FIG. 2B is diameter D1 which is the diameter of the drill bit 12 formed by the retracted bit portions 14. This diameter D1, is slightly smaller than the diameter D2 of the distal end of the support sheath 18. This distal end of the sheath 18 may be formed with the cutting spur 24 configuration of FIG. 1, or the planar end of FIG. 2B. Either way, it is preferred to allow the drilled aperture or passage to have a slightly larger diameter D2, once finished. This allows for easy movement of the drill bit 12 formed as a grasping instrument in FIG. 2A, having an object grasped within the gap 26, back through the formed passage.

Figure 3A:
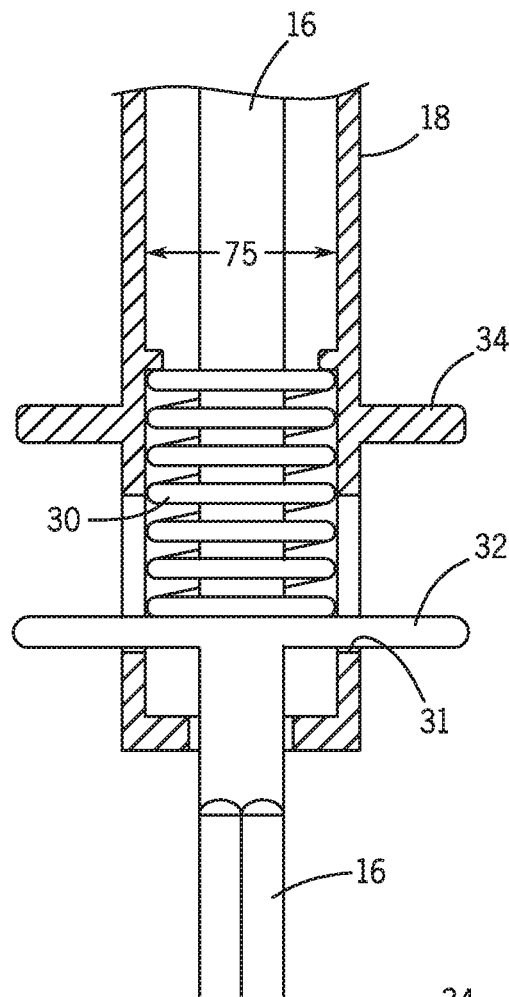
FIG. 3A depicts a sectional view showing a biasing means such as a spring, operatively engaged to maintain the drill bit in the collapsed orientation of FIG. 2B during employment for drilling.
Figure 3B:
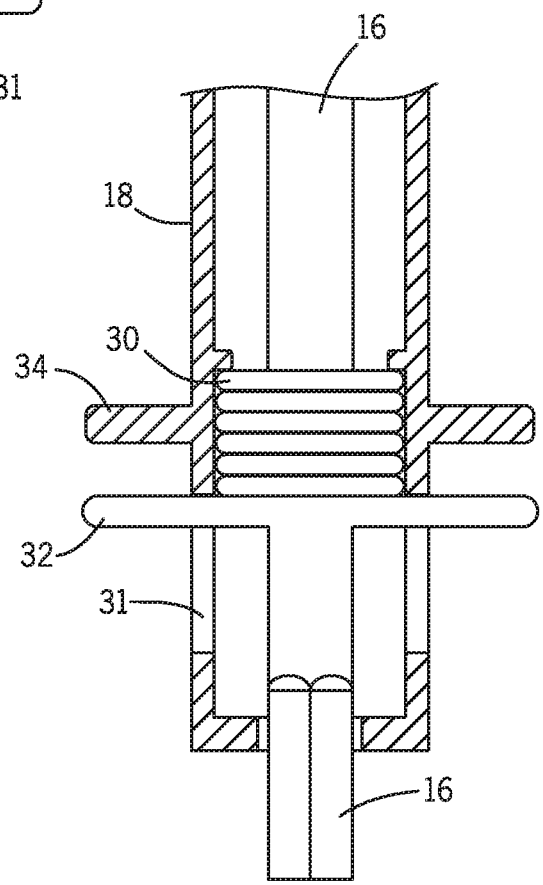
FIG. 3B depicts the device as in FIG. 3A, but showing the biasing spring forced to a collapsed configuration by advancing the drive member forward, which will allow for deployment outside of the sheath and expansion of the drill to the grasping position of FIG. 2A.

FIGS. 3A and 3B depict one mode of imparting a biased contact of the support sheath 18 against the bit portions 14, and for releasing the force forming the biased contact, thereby changing the surgical instrument 10 into an instrument for grasping. As shown, a biasing component 30 (such as a spring) continuously urges the support sheath 18 toward the contact areas 28 of the bit portions 14. To release this force, the user will force a projecting member 32 extending through a slot 31 in the wall of the support sheath 18 which is operatively connected to the drive member 16, and in contact with one end of the biasing component 30, toward a base member 34. This base member 34 is shown as an annular ring projecting from an engagement to the support sheath 18. This concurrently translates the bit portions 14 connected to the distal end of the drive member 16, to project from the distal end of the sheath 18, in the expanded configuration of FIG. 2A. Releasing the force by the user will cause the biasing component 30 to reposition and form the bit portions 14 back to a drill bit 12 configuration, or, to collapse the gap 26 therebetween, and grasp an object for pulling by the device 10.

Figure 4A:
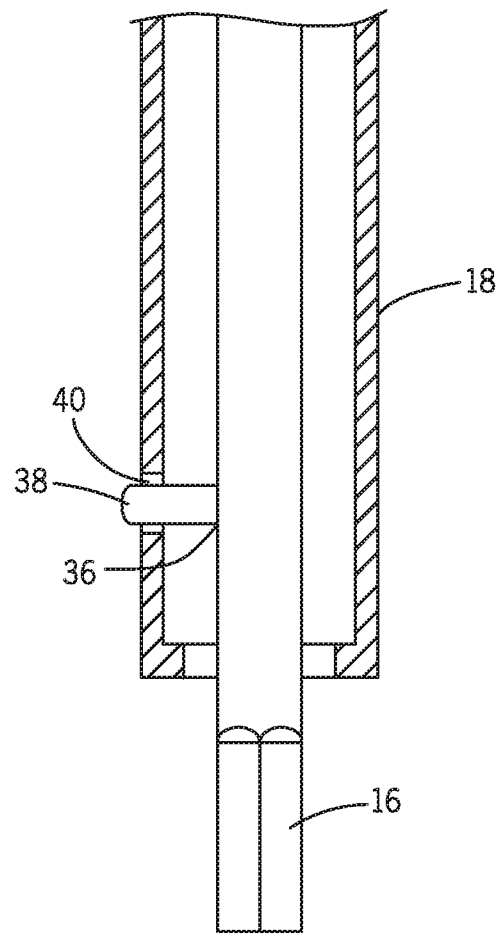
FIG. 4A depicts the device herein having a depressible lock extending from the drive member of the device axially through the support sheath to hold the drill of the device in the collapsed configuration of FIG. 2B.
Figure 4B:
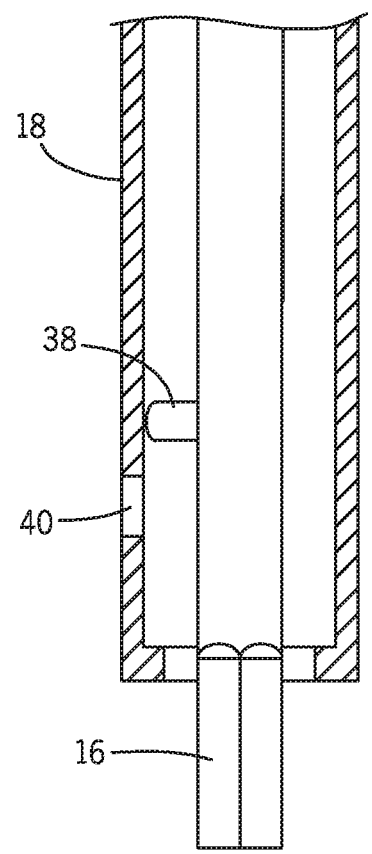
FIG. 4B depicts the device as in FIG. 4A, showing the depressible lock depressed and the drive member translated toward the distal end of the support sheath, thereby forming the device to the configuration of FIG. 2A.

Another example for maintaining the contact between the distal end of the support sheath 18 against the contact areas 28 of the plurality of bit portions 14, is shown in FIGS. 4A and 4B. While not providing any additional biasing force, a lock 36 can be employed to maintain the bit portions 14 attached to the drive member 16, in the collapsed position. As shown, a depressible pin 36 can be engaged through an aperture 40 in the wall of the support sheath 18, thereby locking the drive member 16 and the bit portions 14 engaged thereto in the collapsed position forming a drill bit 12.

Depressing the pin 38 into a slot in the drive member 16, will allow the user to push the drive member 16 toward the distal end of the support sheath 18, and form the drill bit 12 to the grasping configuration such as in FIG. 2A. Pulling the drive member 16 in a direction away from the distal end of the support sheath 18, will cause the bit portions 14 to collapse, and either grasp an intended item, or reform to a drill bit configuration such as in 2B.

Depicted in FIG. 5 is an overhead a view of the distal end of the device 10. Shown is a particularly preferred mode of the device 10 configured to provide support to hold the bit portions forming the bit 12, in place during a drilling procedure. The interior surface of the distal end of the support sheath 18, adjacent the opening 20, is substantially mirrored in shape to that of the respective contact area 28 abutting it. The plurality of substantially shaped intersections of the contact areas 28 with the interior surface of the support sheath 18 provides secure engagement of the support sheath 18 with the plurality of bit portions 14 to hold them in the shape of a drill 12 when force is applied to rotate the surgical instrument 10. In an embodiment, as shown in FIG. 5, the first end (or distal ends) of the drill bit sections 14 may physically touch each other in the collapsed orientation and may not touch either other in the expanded orientation, therein creating the gap 26 in the expanded orientation.

Figure 8:
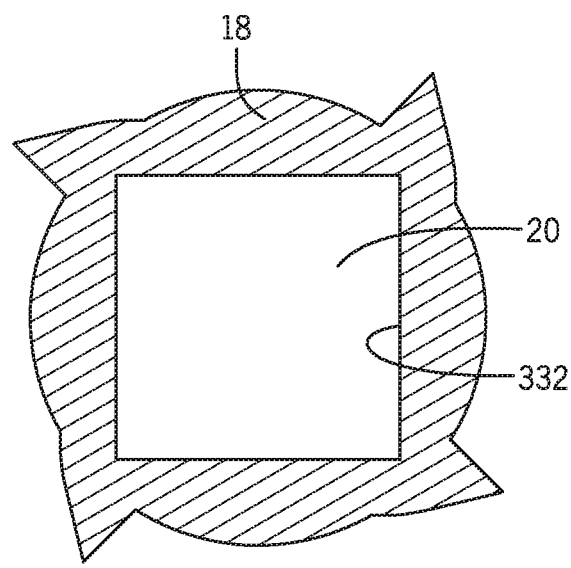
FIG. 8 illustrates a top view of the instrument in the preferred embodiment wherein the square-shaped drill bit is removed from the sheath so that only the top of the sheath is visible.

Referring now to FIGS. 8 and 9, in the preferred embodiment, the drill bit 12 is square-shaped, as opposed to being circular as shown in FIGS. 1, 2A, 2B, 5 and 6). In this embodiment, the opening 20 of the sheath 18 is also square-shaped having preferably four sides 332 (alternative non-circular options are possible). The rotation of the sheath 18 therein rotates the drill bit 12 located within the sheath 18.

Figure 6:
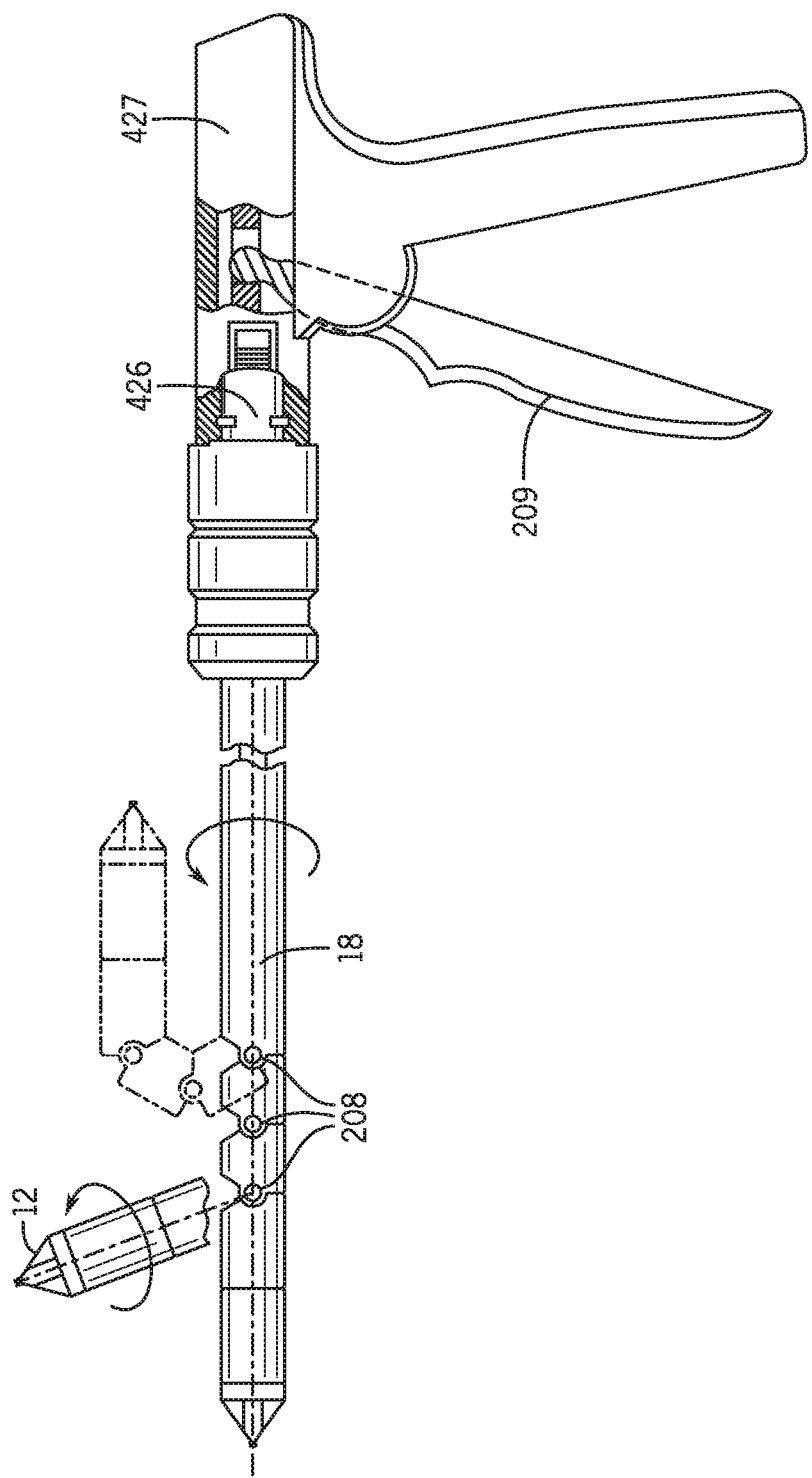
FIG. 6 depicts an alternative embodiment wherein the drill bit and the sheath of the surgical instrument may have joint(s) and may be operated in a non-linear manner for drilling and/or grasping at various angles within the body.

Finally, referring now to FIG. 6, in an embodiment, both the sheath 18 and the drill (either in the collapsed or expanded orientation) may be selectively angled by the surgeon. More specifically, the surgeon may move the surgical instrument 10 from the generally straight orientation as shown in FIG. 1 to a bent orientation as shown in FIG. 6. In the bent orientation the surgeon may more easily drill and or grasp an object within the body. The surgical instrument 10 may therefore be selectively moved between a straight orientation and a bent orientation by activation of a trigger 209. The sheath 18 and the drill bit 12 may articulate as a result of being either segmented and/or as a result of being made of a bendable, non-rigid material. In this embodiment, the sheath 18 may have at least one joint 208. The surgeon operating the trigger 209 may selectively bend the sheath 18 and drill bit 12 at the joint(s) 208 to angle the surgical instrument 1 as necessary.

While all of the fundamental characteristics and features of the combination drill bit and grasping device herein, have been shown and described herein, with reference to particular embodiments thereof, a latitude of modification, various changes and substitutions are intended in the foregoing disclosure and it will be apparent that in some instances, some features of the invention may be employed without a corresponding use of other features without departing from the scope of the invention as set forth. It should also be understood that various substitutions, modifications, and variations may be made by those skilled in the art without departing from the spirit or scope of the invention.

Consequently, all such modifications and variations and substitutions are considered included within the scope of the invention as defined by the following claims.

I claim:

1. A combination surgical drill and remote grasping device comprising:
    an elongated sheath having a first end having an opening, a second end and an interior channel;
    a drill bit having a first end forming a head and a second end wherein the drill bit is partially located within the elongated sheath;
    wherein the drill bit has at least two drill bit sections each having a first end and a second end wherein the drill bit sections together form the drill bit; and
    wherein the drill bit may move from a first orientation wherein the first end of the drill bit sections are located next to each other to a second orientation wherein the first end of the drill bit sections are not located next to each other.

2. The combination surgical drill and remote grasping device of claim 1 wherein the drill bit sections are capable of grasping an object when the drill bit sections are in the second orientation.

3. The combination surgical drill and remote grasping device of claim 1 further comprising:
    a first side and a second side of each of the drill bit sections wherein the first side of each drill bit section has a height which is less than a height of the second side of the same drill bit section.

4. The combination surgical drill and remote grasping device of claim 1 wherein the sheath and the drill bit have a joint and wherein the joint is capable of bending the sheath and the drill bit into a non-liner manner.

5. The combination surgical drill and remote grasping device of claim 1 further comprising:
    an indentation at the first end of each of the drill bit sections wherein each indentation is capable of securing an object to be grasped by the drill bit sections.

6. The combination surgical drill and remote grasping device of claim 1 wherein the drill bit sections move independent of the sheath along an x-axis.

7. The combination surgical drill and remote grasping device of claim 1 further comprising:
    a locking mechanism attached to the sheath wherein the locking mechanism locks the drill bit sections with respect to the sheath.

8. The combination surgical drill and remote grasping device of claim 1 further comprising:
    a biasing member attached to the drill bit sections wherein the biasing member moves the drill bit between the first orientation and the second orientation.

9. The combination surgical drill and remote grasping device of claim 1 wherein the first ends of each of the drill bit sections are triangular.

10. The combination surgical drill and remote grasping device of claim 1 wherein the interior of the sheath is square-shaped.

11. The combination surgical drill and remote grasping device of claim 1 further comprising:
    an extended cutting edge extending outward from the sheath wherein the extended cutting edge rotates with the sheath and is capable of drilling an opening.

12. The combination surgical drill and remote grasping device of claim 1 wherein the sheath and drill bit rotate in unison in the first orientation and are capable of drilling an opening.

13. The combination surgical drill and remote grasping device of claim 1 further comprising:
    an outwardly slanted ridge section at the opening of the first end of the sheath wherein the outwardly slanted ridge section aligns with an extended edge of the head of the drill bit in a flush manner when the drill bit sections are in the first orientation.

14. The combination surgical drill and remote grasping device of claim 1 wherein the combination surgical drill and remote grasping device are made of metal.

* * * * *